(12) United States Patent
Ise et al.

(10) Patent No.: US 6,352,504 B1
(45) Date of Patent: Mar. 5, 2002

(54) PATIENT MONITORING DEVICE

(75) Inventors: Edgar Ise, Lübeck (DE); Rob Spapens, Hilvarenbeek (NL); Christoph Landowski, Stockelsdorf; Markus Rechlin, Hamburg, both of (DE)

(73) Assignee: Dräger Medizintechnik GmbH (DE)

( * ) Notice: Subject to any disclaimer, the term of this patent is extended or adjusted under 35 U.S.C. 154(b) by 0 days.

(21) Appl. No.: 09/415,275

(22) Filed: Oct. 8, 1999

(30) Foreign Application Priority Data

May 19, 1999 (DE) .......................... 199 22 855

(51) Int. Cl.[7] ............................... A61B 5/00
(52) U.S. Cl. .................. 600/300; 600/301; 708/104; 439/928
(58) Field of Search .............. 60/300–301, 481–486, 60/522, 529–538, 544–545, 587; 128/902–903, 897–898; 705/2–3; 708/104–105; 439/928–929

(56) References Cited

U.S. PATENT DOCUMENTS 4,715,385 A    12/1987  Cudahy et al.
5,687,717 A  * 11/1997  Halpern et al. ............. 600/300

* cited by examiner

Primary Examiner—Kevin Shaver
Assistant Examiner—Michael C Astorino
(74) Attorney, Agent, or Firm—McGlew and Tuttle, P.C

(57) ABSTRACT

A device is provided for monitoring patients, which is used to detect and process physiological data of a patient, which are measured by sensors. To make possible the most flexible use possible in patient monitoring, especially the connection of additional special sensors (2) and to ensure simple handling of the device even in the case of transportation, the patient monitoring device has a transportable terminal (8), which has connections (18) for connection to sensors (2) for measuring physiological parameters of the patient and signal processing devices (31, 23, 24, 25) for receiving and processing the sensor signals received, and is provided with a network adapter (26) for forwarding the processed sensor data to a stationary medical workplace (14) with display and alarm devices, as well as one or more expansion modules (9) for the connection of additional desired sensors (2). Wherein the housing (17) of the terminal (8) is provided with a connection mechanism for the positive-locking coupling of the transport display module (7) on one side and with a connection mechanism for the positive-locking coupling of an expansion module (9) for receiving signals of additional sensors (2) on the other side. Electrical contacts (44) are also provided on the terminal (8), the contacts (44) being designed such that they come into connection with complementary contacts (48) on the transport display module (7) and on the expansion module (9) at the time of the coupling of the connection mechanism to establish the electric connection.

26 Claims, 15 Drawing Sheets

PATIENT MONITORING DEVICE

FIELD OF THE INVENTION

The present invention pertains to a device for monitoring patients, which is used to detect and process physiological data of a patient, wherein the physiological data are detected by sensors.

BACKGROUND OF THE INVENTION

Such patient monitoring devices have a terminal associated with a patient, to which one or more sensors for detecting physiological parameters of the patient are to be connected. The terminal receives the electric signals of the sensors and processes same further, e.g., by digitization, calibration and scaling. The sensor data having been subjected to further processing are forwarded from the terminal in steady state to a connected medical workplace, which usually has a display device (e.g., a computer screen) for displaying the patient's vital functions, and additional data entry and data processing devices in order to provide a display of the patient's health status. Furthermore, optical and/or acoustic alarm devices, which alert the hospital personnel concerning critical changes in the patient's status, are usually provided.

Besides the stationary operating state described, in which the terminal is arranged at or near the patient's bed and is connected to the medical workplace via an electronic network, a nonstationary operating state occurs during the transportation of the patient, in which the terminal is not connected to the medical workplace via the electronic network. To ensure the monitoring of the patient during transportation as well, a small, lightweight and mobile display must be provided, which can be connected to the terminal as a transport display module.

The type of the physiological parameters that must be detected in a given patient changes from one patient to the next depending on the diagnosis and the instantaneous health status. From this arises the requirement that different types of sensors must be able to be connected in order to make it possible to detect the desired parameters of the patient monitored in the particular case. It may also be necessary for this, in principle, to provide additional signal reception components for additional special sensors, which are not provided in the terminal.

The handling of such patient monitoring devices, especially the connection of additional or other sensors, or the connection to a transport display module at the time of a change from the stationary operating state to the nonstationary one, must be simple, on the one hand, and highly reliable and dependable, on the other hand, so that such changes in the patient monitoring device can be performed by the hospital personnel with the often necessary rapidity and at the same time in a highly reliable manner.

A patient monitoring device that permits a stationary operating state and a nonstationary operating state has been known from, e.g., U.S. Pat. No. 4,715,385. The prior-art device has a terminal, which is pushed into the housing of a stationary medical workplace in the stationary operating state. In the nonstationary case, i.e., for the transportation of the patient, the terminal is pulled out of the medical workplace and is pushed into the housing of a transport display module, which is open on one side, and is connected to the transport display module via a cable connection. However, this solution is disadvantageous because the insertion of the terminal into the transport display module as a plug-in module fundamentally limits the possibility of expansion of the terminal and the connection of additional components to the terminal is not possible in a simple and compact manner.

SUMMARY AND OBJECTS OF THE INVENTION

The primary object of the present invention is to provide a patient monitoring device in which the terminal can be connected to a transport display module in a simple and reliable manner and which has a compact design and offers possibilities for connecting additional sensors.

According to the present invention, the patient monitoring device has a terminal, which is designed such that its housing is provided on one side with a connection mechanism for the positive-locking coupling of a transport display module and on another side with a connection mechanism for the positive-locking coupling of an expansion module for receiving signals of additional sensors. Furthermore, electric contacts are provided on the terminal on each connection mechanism, the contacts being designed such that they automatically come in connection with complementary contacts on the transport display module or on the expansion module at the time of coupling of the connection mechanism to establish the electric connection to the terminal.

The transport display module can thus be arranged on the terminal in one step by coupling with the connection mechanism, and the necessary electric connection is established simultaneously with the mechanical coupling. Furthermore, the terminal makes possible the coupling of an expansion module on another side of its housing via a corresponding connection mechanism, the expansion module being used to receive and preliminarily process sensor signals of additional special sensors. The patient monitoring device can thus be coordinated with the configuration needed in the acute situation with special sensors by connecting the suitable expansion modules.

In an advantageous embodiment, the housing of the terminal is designed as a flat component with opposite large-area side faces, at which the connection mechanisms for connecting the transport display module and an expansion module are arranged. The ease of handling and the accessibility are improved by the connection mechanisms being arranged on opposite side faces, so that the connection of the transport display module is not interfered with or hindered by the connection of additional expansion modules.

In another advantageous embodiment, an additional connection mechanism corresponding to that on the terminal may be provided on a first expansion module on a side of this expansion module facing away from the terminal in the coupled position, so that an additional expansion module can be coupled with the first expansion module in exactly the same manner as it is coupled directly with the terminal.

In another preferred embodiment, each connection mechanism is designed with a guide pair comprising a guide support and a complementary guide body such that with the terminal standing upright, the guide pair can be brought into engagement by depositing the transport display module and the expansion module (hereinafter occasionally called together by the generic term "auxiliary device") downward in the vertical direction. It is achieved as a result that the auxiliary device can be brought into engagement with the terminal by depositing it from the top next to the terminal, which permits simple handling of the devices by the personnel. In another preferred embodiment, the guide pair is designed such that after the insertion of the guide body, a pivotable connection is first established between the auxiliary device and the terminal, the pivot axis being defined by the longitudinal axis of the guide pair, which is horizontal and parallel to the housing faces in the lower area of the auxiliary device. It is achieved as a result that after depositing the auxiliary device on the terminal, while the auxiliary device is initially still being held slightly obliquely in relation to the terminal, the auxiliary device is fully pivoted at the top to the terminal after the engagement of the guide pair and may be locked there.

This may be achieved, e.g., by the guide pair having a groove and a tongue, which engage one another at the time of insertion, wherein the groove is designed as a one-sided undercut in the housing face and the tongue engages the groove from the top during insertion. In this advantageous embodiment, the groove and tongue of the connection mechanism allow for a pivotability around a pivot axis at right angles to the vertical direction of deposition and in parallel to the face of the housing of the terminal. After the insertion of the auxiliary device and engagement of the tongue-and-groove connection, the auxiliary device may be pivoted at the top to the terminal into the coupled position.

To further improve centering, an additional centering pair is advantageously provided for this, which has a conical centering body and a conical centering fit, which extend essentially at right angles to the housing faces and are arranged at widely spaced locations from the pivot axis of the guide pair, so that they are pushed one into the other at the time of pivoting of the auxiliary device onto the terminal into the coupled end position and improve the correct alignment in the end position due to their conical design.

To simplify the handling of the connection mechanism, the guide body and the guide recess are provided with additional guide means such that the auxiliary device to be attached is guided into the correct position during deposition next to the terminal and the groove and tongue are thus guided into engagement with one another on the lower end sides by the guide body and the guide recess. This may be accomplished in a simple manner by, e.g., the guide body being provided with downwardly tapering side walls due to a downwardly increasing projection and by the complementary guide recess being provided with downwardly tapering side walls, so that the connection mechanism is guided by the complementarily conical side faces of the guide and the groove and tongue engage one another.

In another embodiment of the present invention, the device is provided with a carrying device for patient-related use. This embodiment is advantageous if standardized profiles ate to be used to hold the device and good readability must be ensured. This embodiment is preferably suitable for terminals for patient monitoring, but may also be used for other medical devices that are used at the patient. This embodiment has a transport grip for carrying the terminal by the personnel, on the one hand, and it is also provided with recesses which make it possible to hang the terminal onto a circular tube or a standardized fastening rail. Such standardized profiles, namely, rails or circular tubes, are used in hospitals to hold medical devices. Wall rails are usually mounted at levels of 50 cm or 140 cm above floor level and have a standardized rectangular cross section. Circular tubes usually have an external diameter of 25 mm or 38 mm; they also occur on the head and foot sides of the hospital beds. To make possible the reliable and possibly variable holding of the terminal on such profiles, the carrying device is preferably provided with at least one strut, which has in its contour at least a first recess for receiving a horizontal fastening rail in a positive-locking manner and at least a second recess for placement on a horizontal circular tube.

At least two first recesses are preferably present, one of them being arranged such that the terminal is held essentially in the vertical alignment on the rail, while the other is arranged such that the terminal is held on the rail obliquely in relation to the vertical. This latter possibility of mounting the terminal obliquely, e.g., at an angle of about 30° to about 60°, and especially about 45°, is especially advantageous if the transport display module is connected to the terminal and the oblique position of the terminal with the transport display module permits better readability of the display screen.

The strut, of which there is at least one, is preferably arranged obliquely on the top side of the housing of the terminal, so that, with the terminal standing upright, it projects beyond the base of the housing of the terminal in the projection into the horizontal plane. The recess for the vertical holding of the terminal is preferably arranged in the strut such that it is likewise located outside the base of the housing of the terminal in the projection into the horizontal plane.

The second recess for placement on a horizontal circular tube is preferably made in one piece with the strut such that it surrounds the circular tube to the extent that it holds the terminal in the vertical alignment on the circular tube when the housing of the terminal is supported at least at one additional point in the vertically hanging position.

These particularly preferred embodiments of the present invention with the carrying device explained make possible an especially versatile and convenient handling of the terminal and make it possible to arrange it in many variable ways, so that the position of the terminal can be optimally adapted to the conditions of the moment.

The various features of novelty which characterize the invention are pointed out with particularity in the claims annexed to and forming apart of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 15A is a sectional side view of the terminal that is held on a rail in the vertical position with the carrying device.

DESCRIPTION OF THE PREFERRED EMBODIMENTS

Figure 1A:
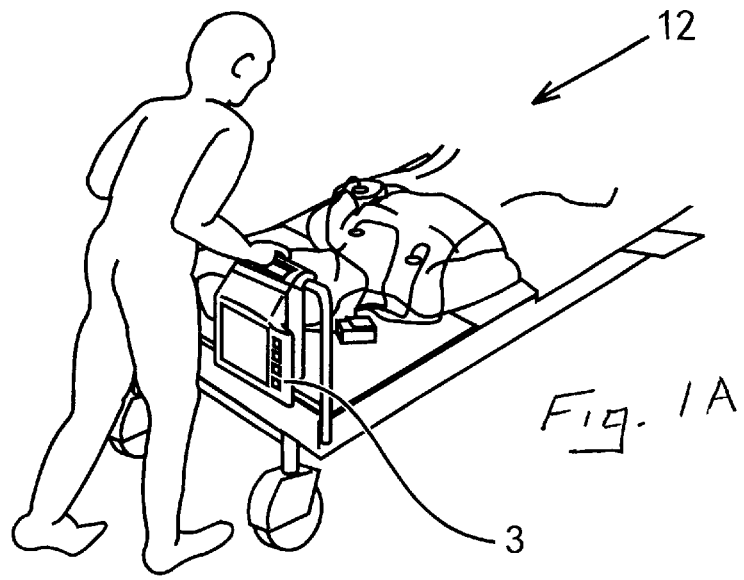
FIG. 1A is a schematic representation of an operating state of a patient monitoring device.
Figure 1B:
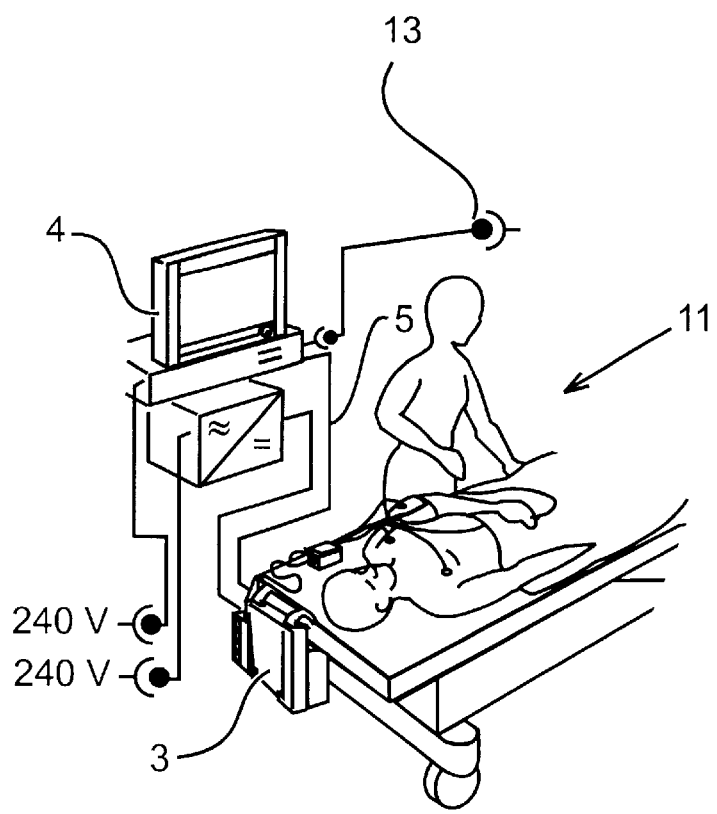
FIG. 1B is a schematic representation of another operating state of a patient monitoring device.

Referring to the drawings in particular, FIGS. 1A and 1B schematically show various operating states of the patient monitoring device 3. The stationary operating state is shown in FIG. 1B, in which a connection of the patient monitoring device 3 to a medical workplace 4 is established via a connection line 5, is shown in the lower part under the reference number 11. The medical workplace 4 is integrated within another, higher network 13, which connects the medical workplaces to one another and to a center.

The nonstationary operating state 12, in which the patient is being transported and in which there is no connection to stationary networks, so that no display of data at the medical workplace is possible and a transport display module is therefore needed at the patient monitoring device 3, is shown schematically in FIG. 1A.

Figure 2:
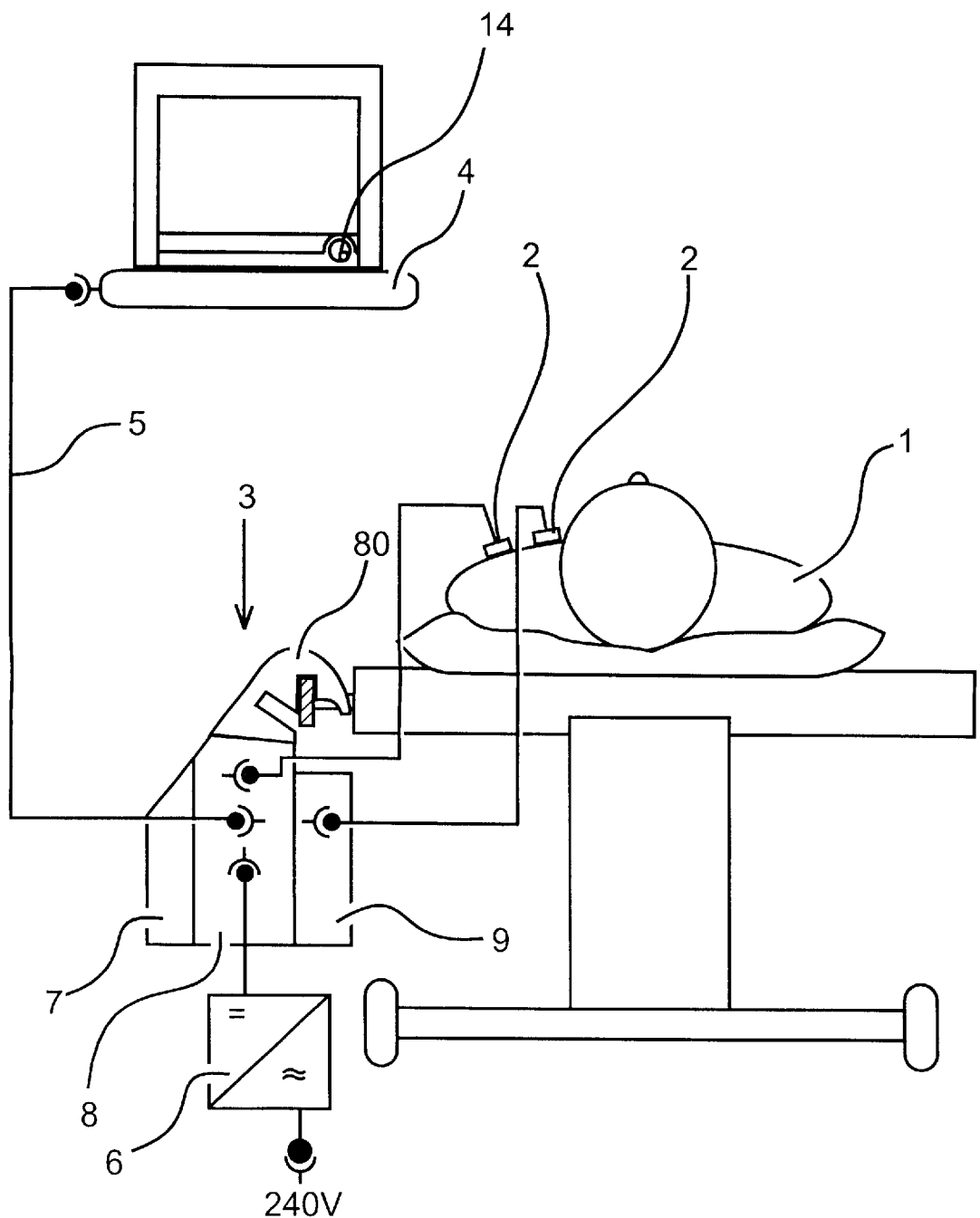
FIG. 2 is a schematic block diagram of a patient monitoring device in the stationary state.

FIG. 2 shows a schematic diagram of the patient monitoring device 3 in the stationary state. The patient monitoring device 3 has a terminal 8, to which an expansion module 9 and in this case also a transport display module 7 are connected. The patient monitoring device 3 is connected to a plurality of sensors 2, which receive measured values from the patient 1, e.g., blood pressure data, ECG values and a plurality of other physiological parameters. Some of the sensors 2 are directly connected to the terminal 8, which receives the sensor signals and subjects them to further processing. Other sensors 2 are connected to the expansion module 9, which receives the sensor signals of special sensors 2 and prepares them for further processing before they are forwarded to the terminal 8.

In the stationary operating state shown in FIG. 2, the patient monitoring device 3 is supplied by an external power supply unit 6. Furthermore, the patient monitoring device 3 is connected to the stationary medical workplace 4 via a connection line 5. The medical workplace 4 has a display screen and an operating element 14 and is provided with data processing capacity for processing the data from the terminal 8 and is integrated within a higher network. A carrying device 80 is located on the terminal 8.

Figure 4:
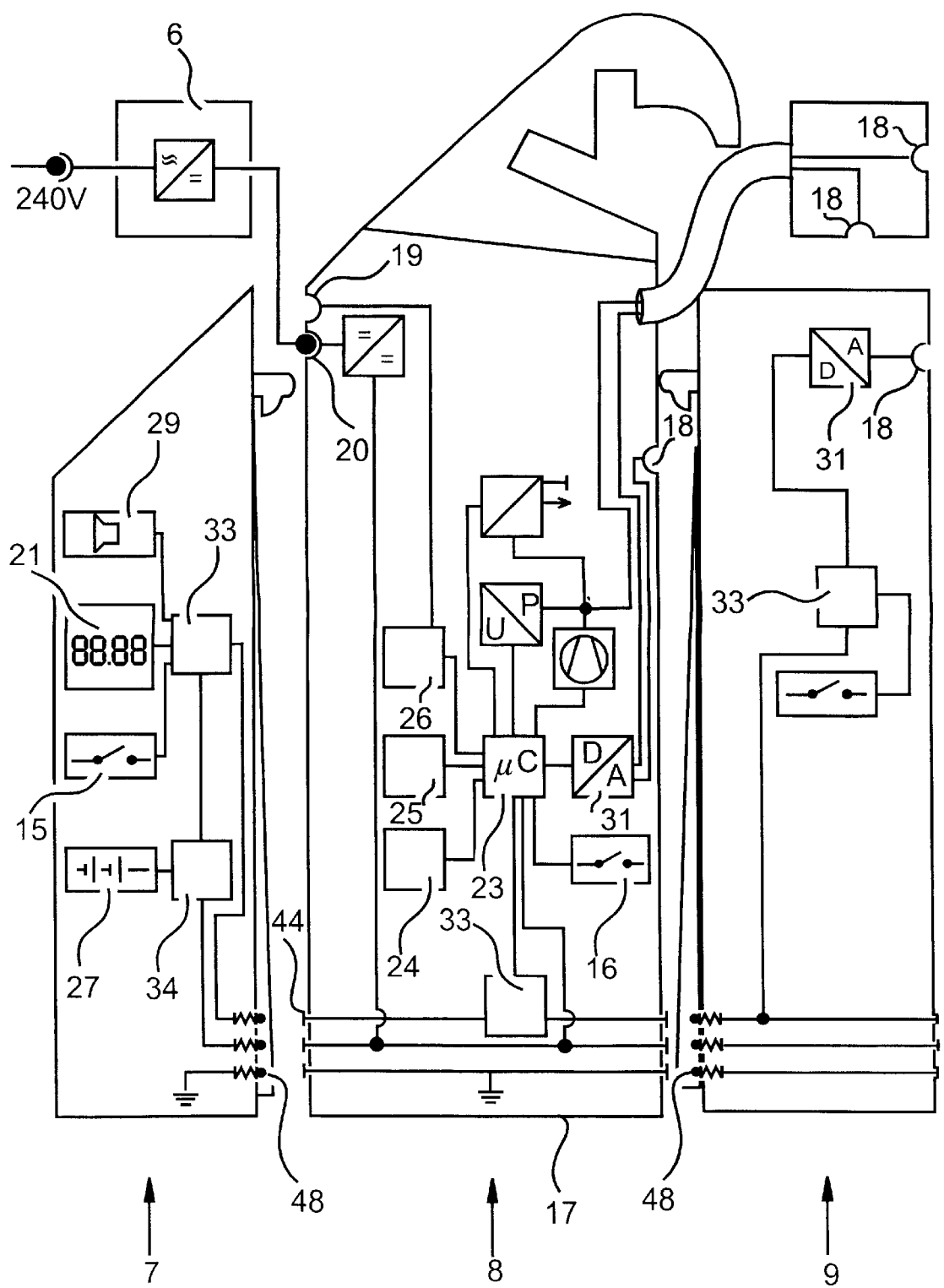
FIG. 4 is a block diagram of a patient monitoring device.

FIG. 4 shows a schematic sectional view of the components, wherein individual circuit components are shown in the form of a block diagram.

In the housing 17, the terminal 8 has a microprocessor 23, a permanent memory 24 and a volatile working memory 25. Sensor signals are received via connections 18 for connecting the sensors 2, and additional signals are optionally fed into the terminal 8 via contact connections 48 if the transport display module 7 or the expansion module 9 is connected. The signals received from the sensors 2 via the connections 18 are converted in an analog-digital converter 31 and are subjected to further processing in the microprocessor 23 and via a network adapter 26, they finally reach the output 19, at which the terminal 8 is connected to the electronic network 13. Signals are correspondingly also received by the expansion module 9 from sensors 2 connected to connections 18, they are converted in the analog-digital converter 31 and are forwarded via the communications unit 33 and to the contacts 48, which are in connection with corresponding contact elements on the terminal 8 when the expansion module 9 is coupled with the terminal 8.

The terminal 8 is supplied with electric power from the power supply unit 6 via the input 20 in the stationary operating state 11. The unit 34 controls the loading and unloading process corresponding to the stationary or nonstationary operating state 11 or 12.

The transport display module 7 has a battery 27 for energy supply, a display 21 as well as an acoustic signal generator 29 and operating elements 15. The signals are forwarded via a communications unit 33.

Figure 5:
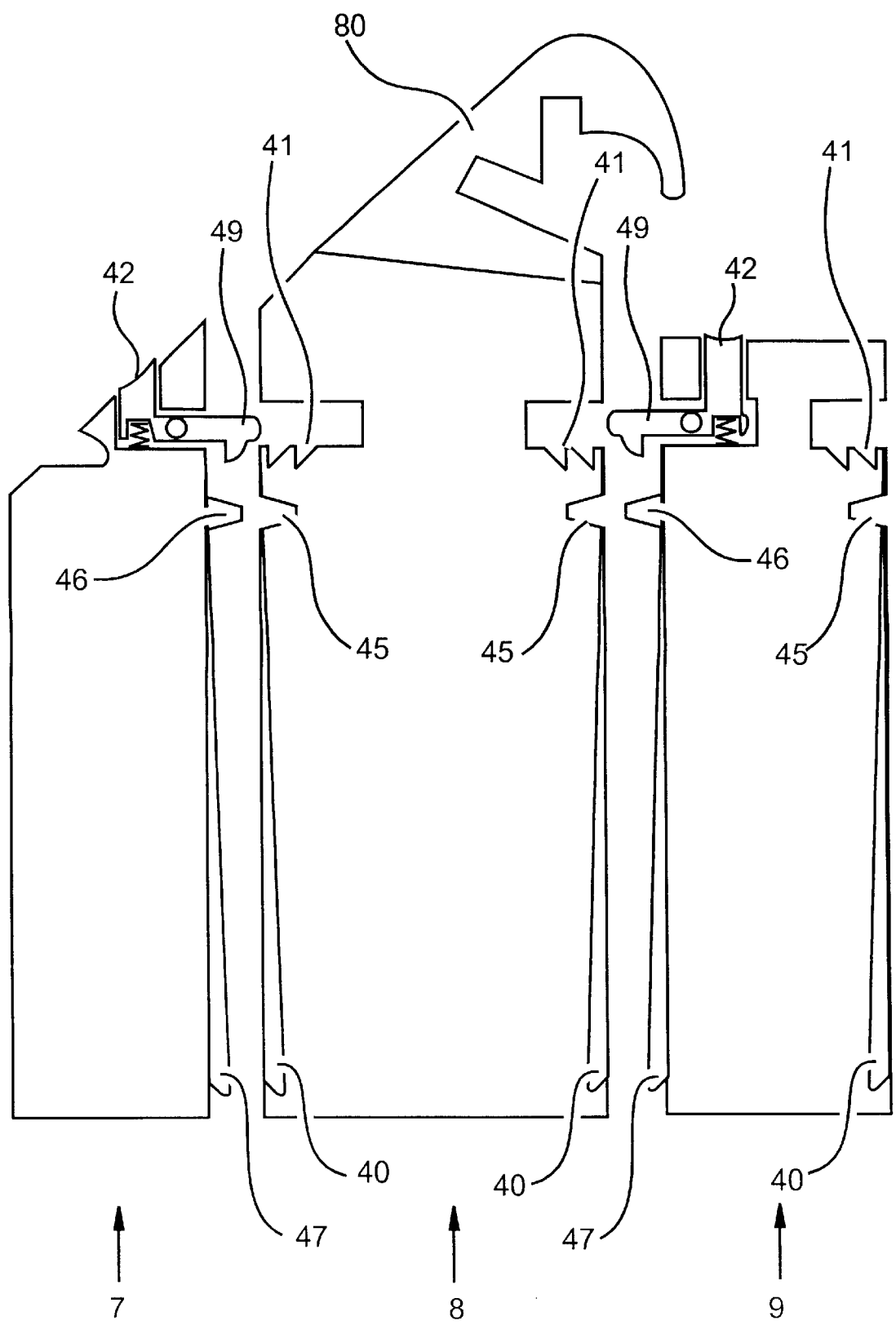
FIG. 5 is a sectional side view of the patient monitoring device with terminal and the auxiliary devices standing next to it.

The connection mechanism for the positive-locking coupling of the expansion module 9 and of the transport display module 7 with the terminal 8 is schematically shown in FIG. 5. The connection mechanism has a guide pair comprising a guide body 47 on the transport display module 7 or on the expansion module 9 as well as a respective complementary guide support 40 on the terminal 8. In the embodiment shown, the guide body 47 is provided at the bottom with a tongue, which projects from the front face of the transport display module 7 and whose lower edge extends in parallel to the lower edge of the housing. The guide support 40 is provided with a complementary groove for receiving the tongue. The guide pair 40, 47 on the terminal 8 and on the auxiliary device 7 or 9 is designed such that the auxiliary device 7 or 9 can be brought into engagement with the terminal 8 standing upright by depositing the auxiliary device 7 or 8 downward in the vertical, direction, i.e., the tongue on the guide body 47 is inserted into the groove of the guide support 40 by depositing the auxiliary device in the downward direction in a slightly oblique position. The tongue and groove of the guide pair 40, 47 are designed such that they permit pivoting of the auxiliary device 7 or 9 against the terminal 8, the pivot axis being at right angles to the vertical direction and parallel to the surface of the housing of the terminal 8, it being namely defined by the longitudinal axis of the tongue.

The tongue forms below in the guide support 40 a one-sided undercut in the housing surface of the terminal 8, with which the tongue of the guide body 47 of the auxiliary device can be brought into engagement.

In such a design of the guide pair of the connection mechanism, pivotability of the auxiliary device 7 or 9 in relation to the terminal 8 is ensured if the auxiliary device 7 or 9 is deposited at the terminal 8 in a slightly oblique position, so that its tongue on the guide body 47 engages the groove in the guide support 40 of the terminal 8. By subsequently pivoting the auxiliary device 7 or 9 at the top in relation to the terminal 8, the auxiliary device 7 or 9 is brought into the completely coupled position.

Figure 3:
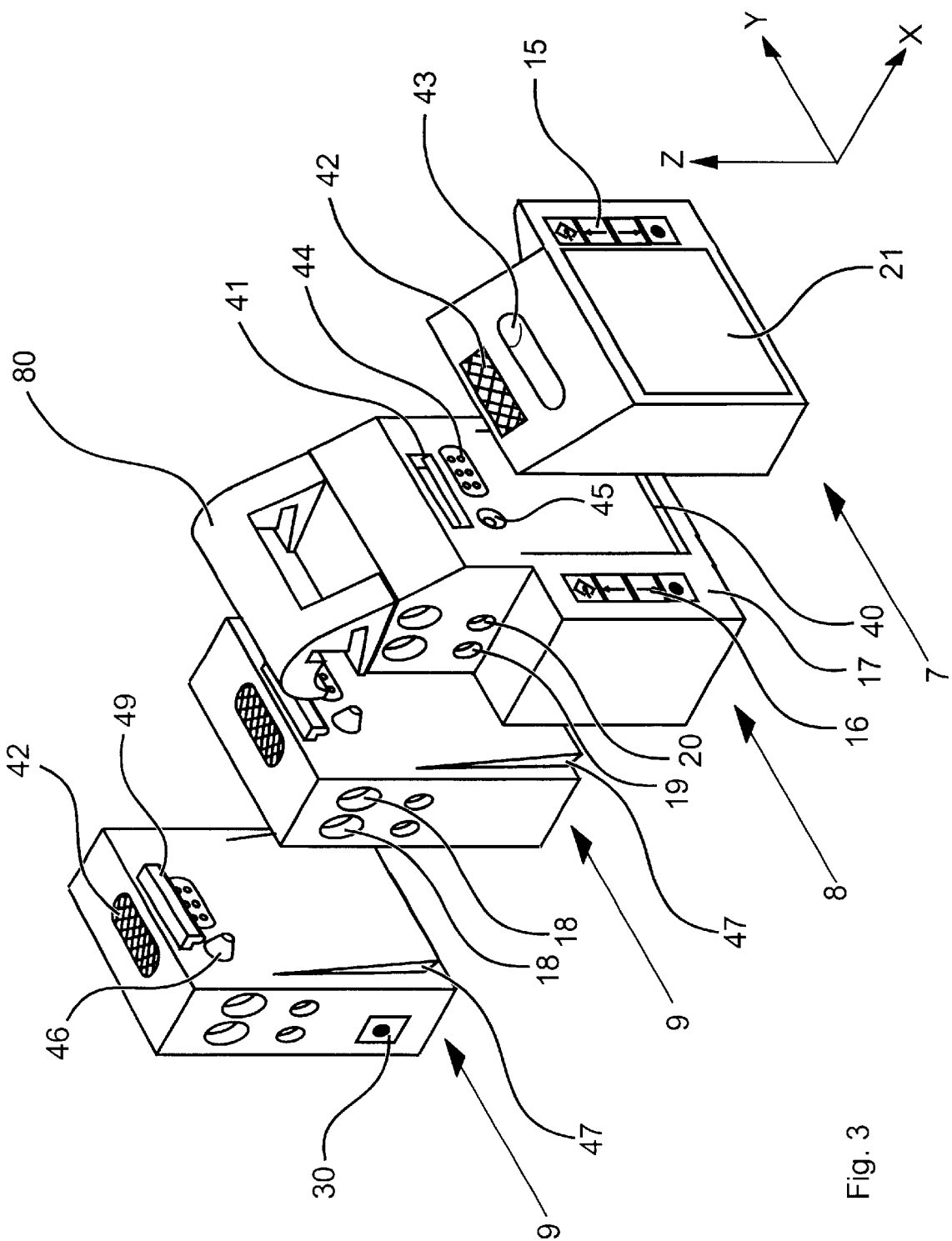
FIG. 3 is a perspective view of a patient monitoring device with device components shown next to one another.

FIG. 3 also shows the perspective view of the guide body 47 and the guide support 40, in which the terminal 8 is shown separately next to the transport display module 7 and, on the other side, next to a first expansion module 9 and an additional expansion module 9.

An additional centering pair, which can be seen, e.g., in FIG. 5 and comprises a conical centering body 46 and a complementary centering fit 45, is provided for suitable guiding and positioning in the coupled end position of the connection mechanism, the centering body 46 projecting essentially at right angles from the housing wall, so that it is guided into the complementary centering fit 45 during the pivoting movement of the auxiliary device 7 or 9 against the terminal 8 and as a result ensures the predetermined final positioning of the auxiliary device 7 or 9 in the coupled position of the connection mechanism.

To facilitate the fitting together of the guide body 47 and the guide support 40, they are designed as follows. As is shown in the cross-sectional view in FIG. 5, the tongue on the auxiliary device 7 or 9 is provided at the lower edge of a guide body 47 rising uniformly from top to bottom and the guide support 40 is formed by a corresponding complementary recess in the housing wall of the terminal 8, whose depth increases from top to bottom and which is provided with a groove at the lower edge. It can also be recognized from the top view in FIG. 6 that the guide support 40, whose depth increases in the downward direction, is limited by side walls 51, which in turn taper in the downward direction. The guide body 47 correspondingly also has complementary side walls, which are arranged essentially at right angles to the housing surface and whose distance from one another correspondingly decreases in the downward direction. The tapering side walls 51 thus ensure a central alignment or centering of the auxiliary device at the terminal 8 when the auxiliary device is inserted by lowering at the terminal 8, the side faces of the guide body 47 being guided at the auxiliary device by the complementary side walls 51 of the recess 50 on the terminal 8 during the downward movement of the auxiliary device 7 or 9 into the central position at the terminal 8.

Furthermore, each connection mechanism is provided with a claw 49 for locking. This claw 49 can be recognized, e.g., in FIG. 5. The claw 49 on the transport display module 7 and on the expansion module 9 is provided in the projecting area with a locking element, which can engage opposing flanks 41 in the other part of the connection mechanism. The claw 49 is mounted pivotably via a joint in the housing, so that the locking elements can be engaged with and disengaged from the opposing flanks 41. The claw 49 is pretensioned by a spring element in the closed position, in which it is snapped in behind an opposing flank 41. To release the claw 49, it is provided with a pressing surface 42, which lies exposed on the housing and is arranged on the other side of the pivot axis in relation to the locking element, so that the claw 49 can be disengaged from the opposing flanks 41 against the action of the spring element by manually pressing the pressing surface 42 and the recessed grip 43. The locking element is provided at the claw 49 with an oblique flank in the front and with a vertical flank in the rear, so that the claw 49 is pivoted when it is pushed into the opening provided with the opposing flanks 41 by the oblique flank of the locking element sliding up and is thus brought beyond the opposing flank 41, and the locking element subsequently snaps in behind the opposing flank 41 by the action of the spring element. The spring element, which acts on the claw 49, does not need to be designed as a coil spring, as is schematically shown, but it may be formed by any desired elastic component on the claw 49.

The opposing flanks 41 for the claw 49 are provided with two opposing flanks 41 located one behind the other in the exemplary embodiment shown, so that the claw 49 can be locked in two positions on the housing of the terminal 8.

Figure 7:
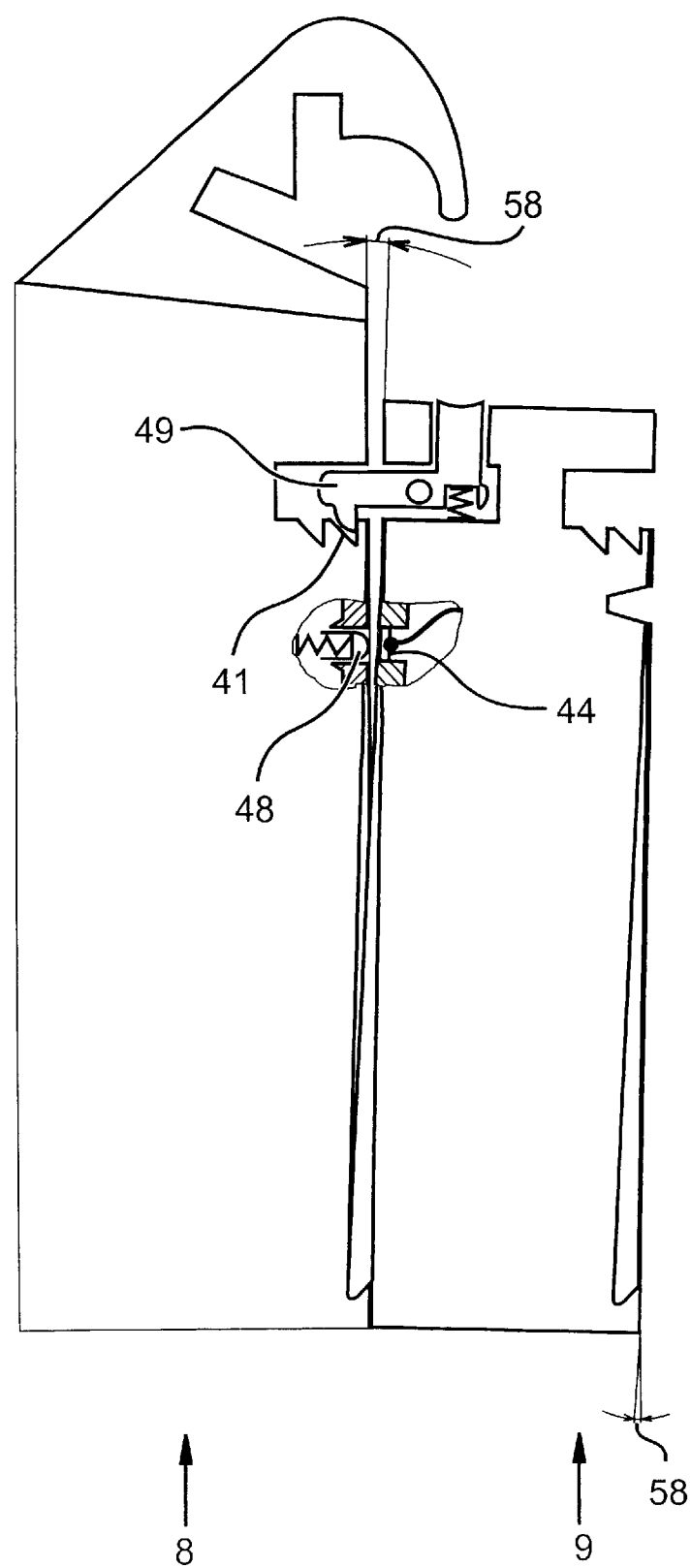
FIG. 7 is a sectional side view of the terminal with a coupled expansion module.
Figure 8:
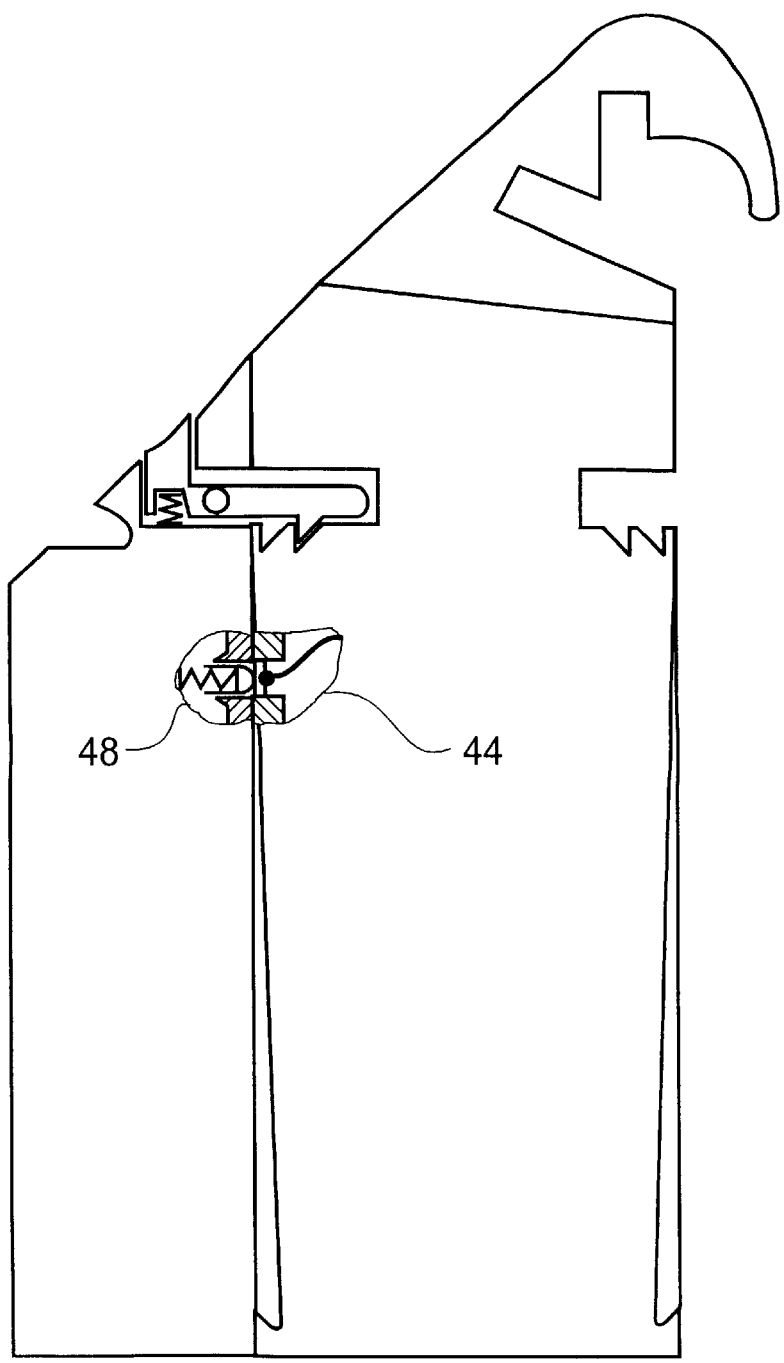
FIG. 8 is a sectional side view of the terminal with a coupled transport display module.

The terminal 8 and the expansion module 9 are shown in FIG. 7 in a secured position, in which the claw 49 has snapped in behind the first opposing flank 41. FIG. 8 shows the locked coupled position of the connection mechanism. The transport display module 7 is aligned in parallel to the terminal 8 in this coupled position. In the secured position shown in FIG. 7, a shift angle 58 is still present between the surfaces of the terminal 8 and the expansion module 9. The secured position ensures that the transport display module 8 or the expansion module 9 will be held in a position close to the terminal 8 in the case of failure of the locking in the rear opposing flank 41, i.e., when the user does not pivot the transport display module 7 or the expansion module 9 against the terminal 8 firmly enough, so that the locking element of the claw 49 does not become locked behind the opposing flank 41 located farther in the rear, so that the device will at least be fixed behind the opposing flank 41 located farther in the front and can thus be brought into the final, locked position by pressing repeatedly. There is no electric connection yet between the contacts 44 and 48 in the secured position.

Figure 6:
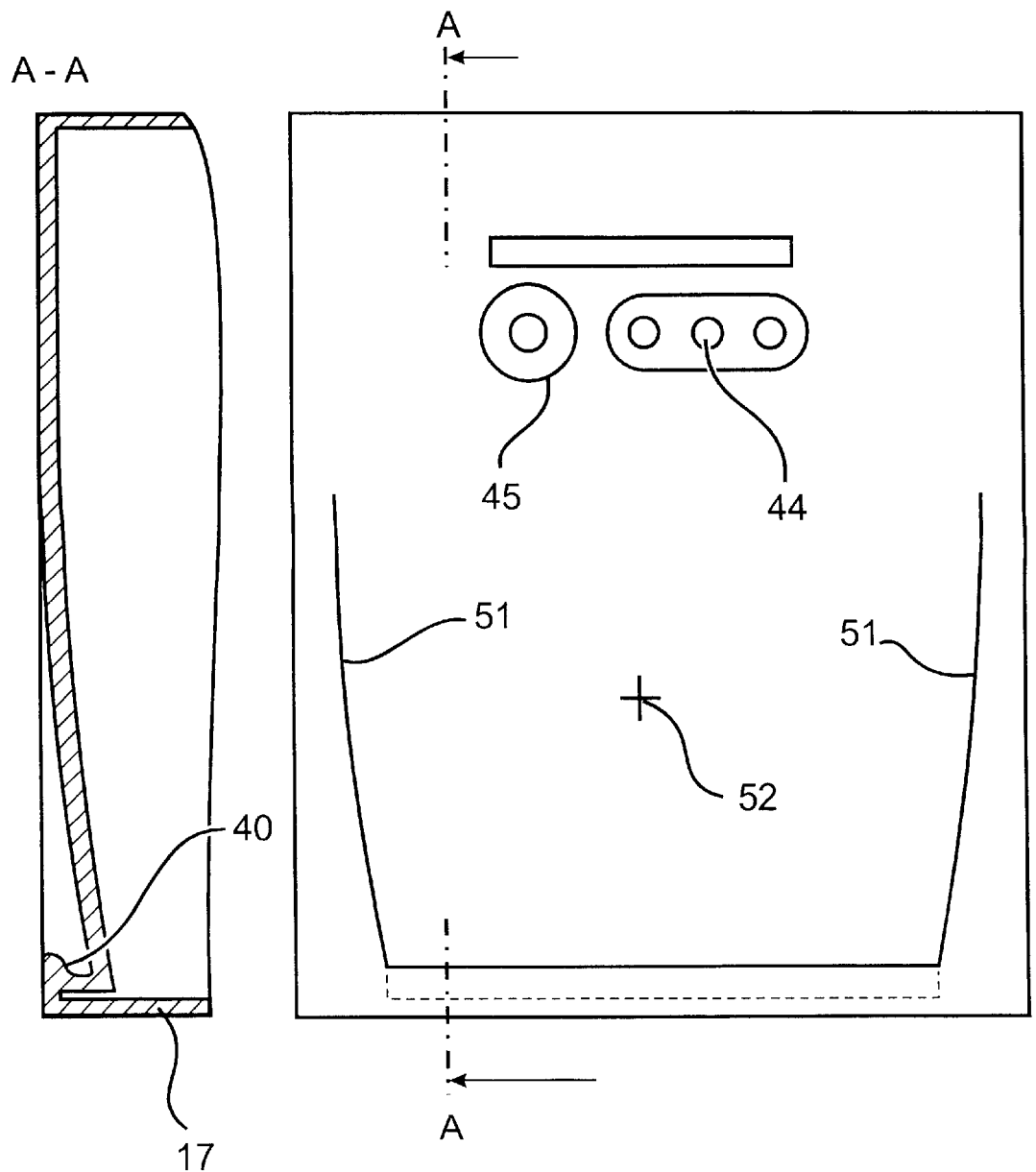
FIG. 6 is a top view and a sectional view along plane A—A of a side face of the housing of the terminal, which side face carries a connection mechanism.

Simultaneously with the mechanical coupling of the connection mechanism, an electric connection is established between the auxiliary device 7, 9 and the terminal 8. To achieve this, contacts 48 are provided on the terminal 8, which are formed by three elastically mounted contact pins in the exemplary embodiment shown. Corresponding complementary opposite contacts 44 (see FIGS. 6 and 7) are provided on the opposite part. Whether the terminal 8 is provided with the contacts 48 and the expansion module 9 with the complementary contacts 44 or the other way around is irrelevant. As can be seen in FIG. 3 or FIG. 6, the contacts 44 are located above the guide support 40 between the side walls 51.

To prevent an incorrect connection of contacts that do not belong together, the contacts 44, 48 are designed such that an electric connection is established between the contacts 44, 48 only when the connection mechanism has brought about a sufficient centering of the terminal 8 and the auxiliary device 7, 9 with one another. This is achieved, e.g., by the contacts being arranged close to the centering pair 45, 46. Furthermore, the spring deflection of the contact pins of the contacts 48 is small for this compared with the height of the centering body 46, so that the centering will have essentially already taken place when the contacts 44, 48 come into connection with one another for the first time.

Figure 9:
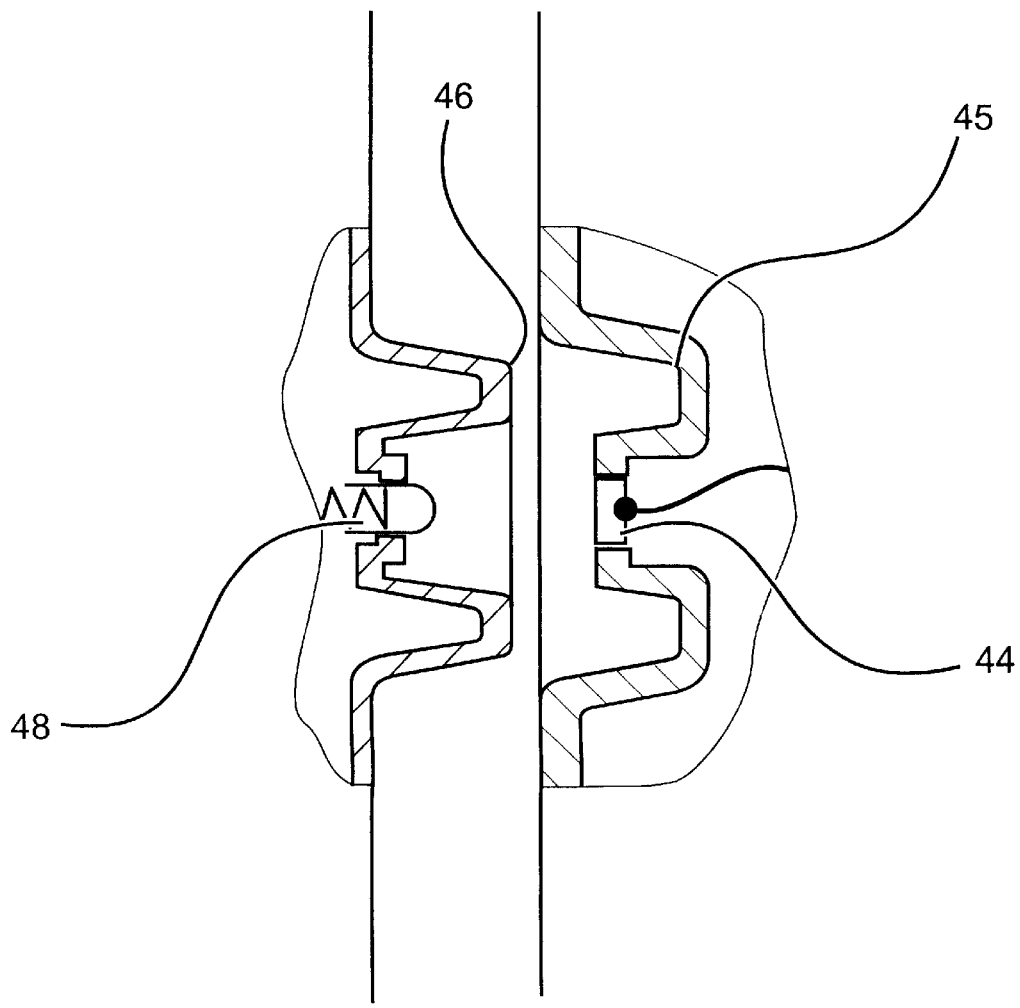
FIG. 9 is a sectional lateral detail view of a centering pair of the connection mechanism.

In an alternative embodiment, which is shown in FIG. 9, the respective contacts 44 and 48 are arranged in the centering fit 45 and in the centering body 46, respectively.

As is shown in FIG. 3, the terminal 8 may be provided on at least one side with operating and display elements 16, which are preferably arranged on the terminal 8 such that they laterally project over the contour of the transport display module 7 in the coupled position of this module, so that the operating and display elements 16 are accessible in a simple manner. A projection with operating and display elements 15 may be correspondingly also provided on the transport display module 7 on the opposite side.

Figure 10:
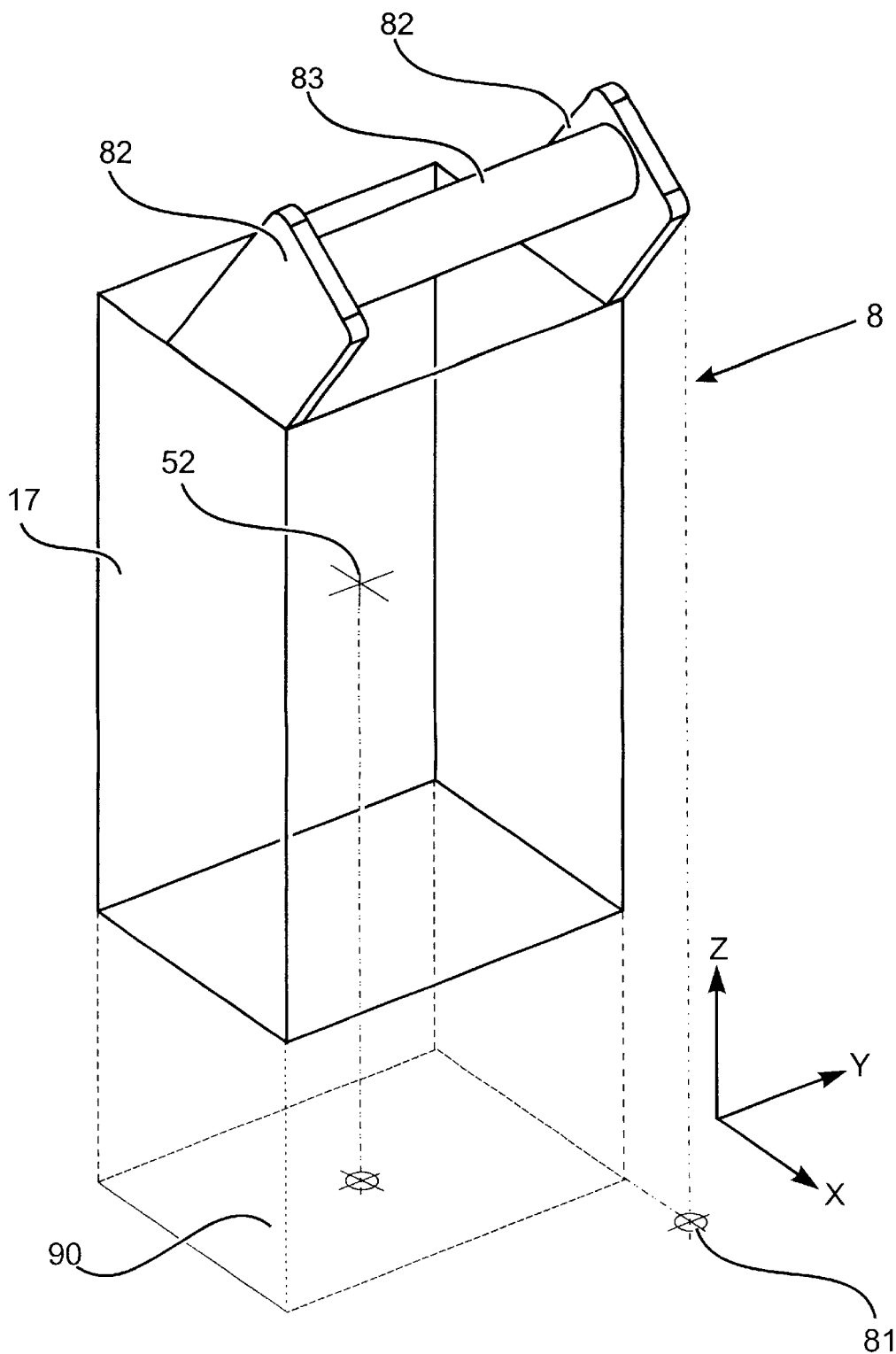
FIG. 10 is a schematic view of the terminal with a carrying device.

FIG. 10 shows a schematic representation of a carrying device for the terminal 8. Two opposite struts 82, which carry a transport grip 83, are arranged at the top of the housing 17 of the terminal 8 (the housing being shown in a greatly simplified form). The struts 82 extend slightly obliquely in relation to the housing 17 of the terminal 8, so that an upper end area of the struts 82 projects beyond the projected base 90 of the housing 17 in the projection into the horizontal plane.

In a preferred embodiment of the present invention, the carrying device is designed such that it makes possible a convenient transportation of the terminal 8 by the transport grip 83, on the one hand, and makes it possible, on the other hand, to securely hold the terminal 8 by the fastening rails or circular tubes intended for this purpose. Such rails with standardized rectangular cross-sectional dimensions, extending horizontally on the walls, are arranged in hospitals in order to make it possible to suspend devices. Horizontally extending circular tubes are occasionally also present for this purpose; circular tubes are likewise present at the foot and head ends of most hospital beds and may also be used to suspend devices.

Figure 11:
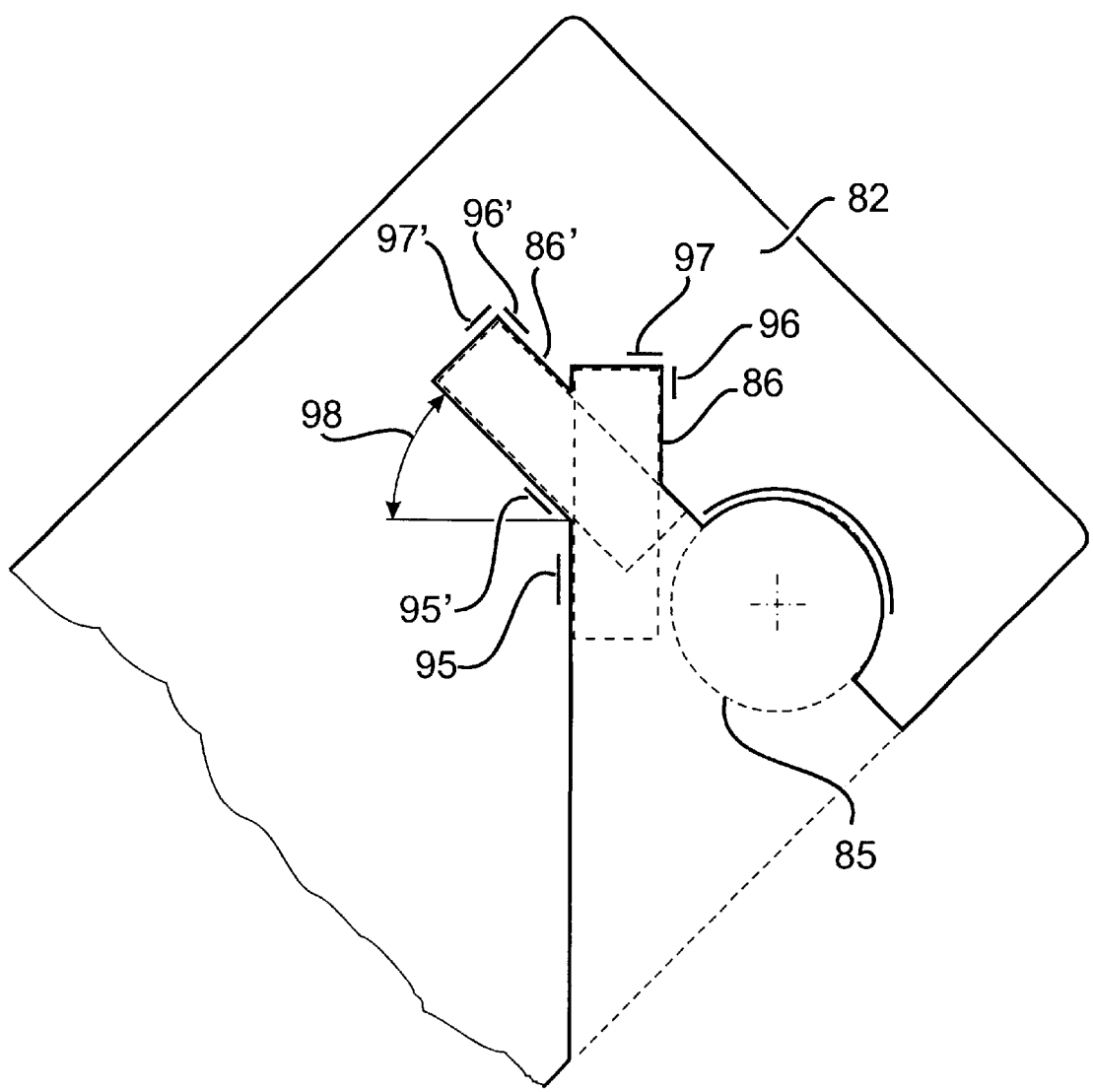
FIG. 11 is a side view of a strut of the carrying device with profile bodies inserted into the recesses.

To make it possible to hold the terminal 8 as flexibly as possible, the struts 82 are provided with at least one first complementary recess 86, 86' for the positive-locking mounting of a horizontal fastening rail 110, and with at least one second recess 85 for placement on a horizontal circular tube 111, as is shown in the schematic representation in FIG. 11, which shows a top view of the strut 82 at right angles to the horizontal course of a fastening rail 110.

Two first recesses 86 and 86' are provided in the embodiment shown, the first of them being provided for engagement with the rectangular fastening rail 110, such that the terminal 8 hangs vertically aligned with the longitudinal sides of the fastening rail 110, as is shown in FIG. 15.

Figure 13A:
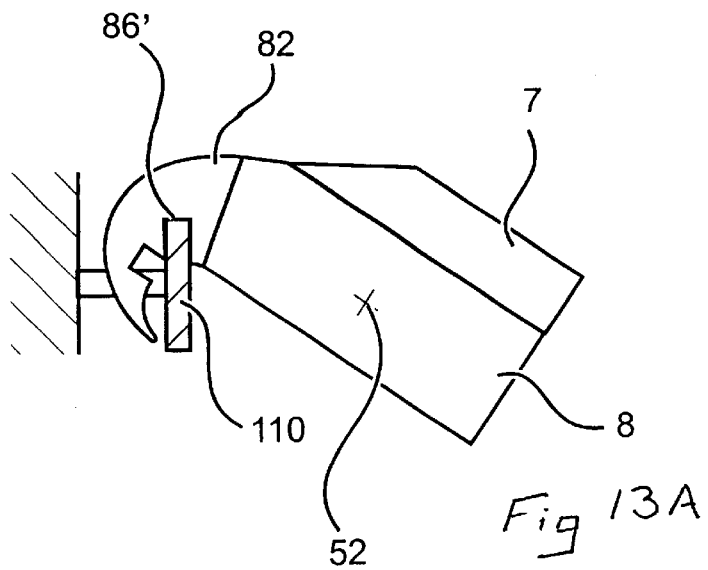
FIG. 13A is a sectional side view of the terminal that is suspended on a rail with the carrying device in the oblique position.
Figure 13B:
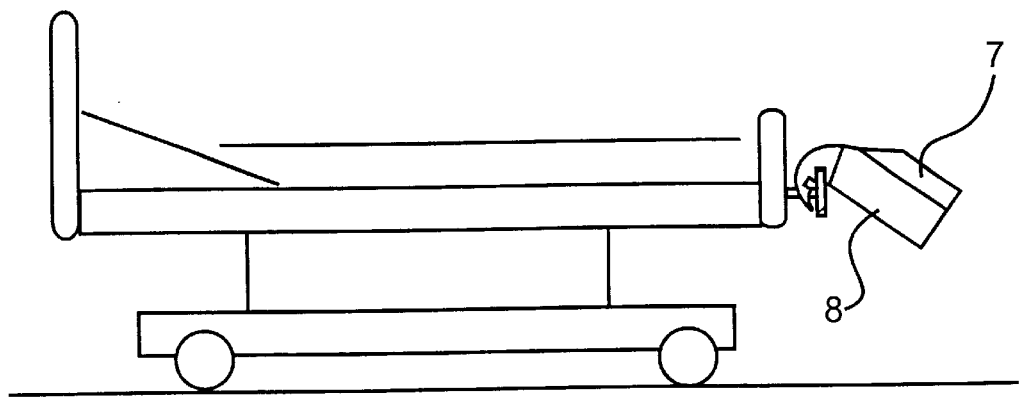
FIG. 13B is a sectional side view of the terminal that is suspended on a rail with the carrying device in the oblique position and also showing the position of the patients bed.

Another first recess 86' is arranged on the strut 82 such that it can surround the fastening rail 110 in a positive-locking manner, in which case the terminal 8 is then suspended in an oblique position at an angle 98 in relation to the vertical. This suspension is shown in FIGS. 13A and 13b. This is especially advantageous if a transport display module 7 is coupled with the terminal 8 and the oblique position of the display screen on the transport display module 7 permits better readability.

Figure 14A:
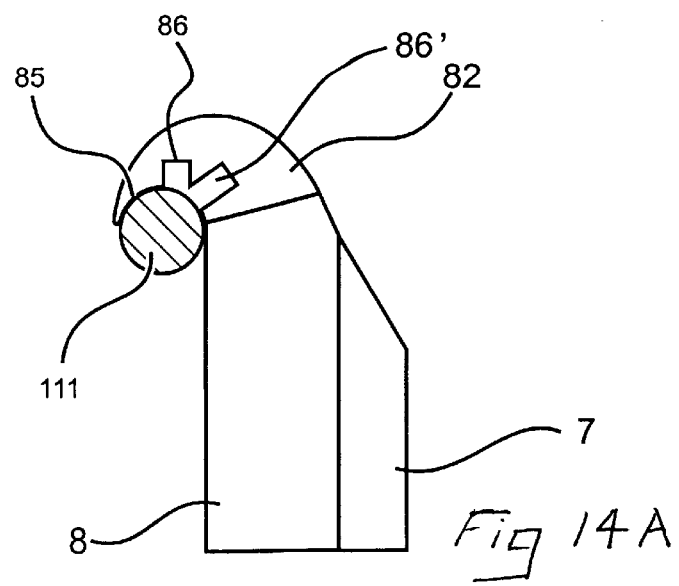
FIG. 14A is a sectional view of the terminal that is held on a circular tube with the carrying device.
Figure 14B:
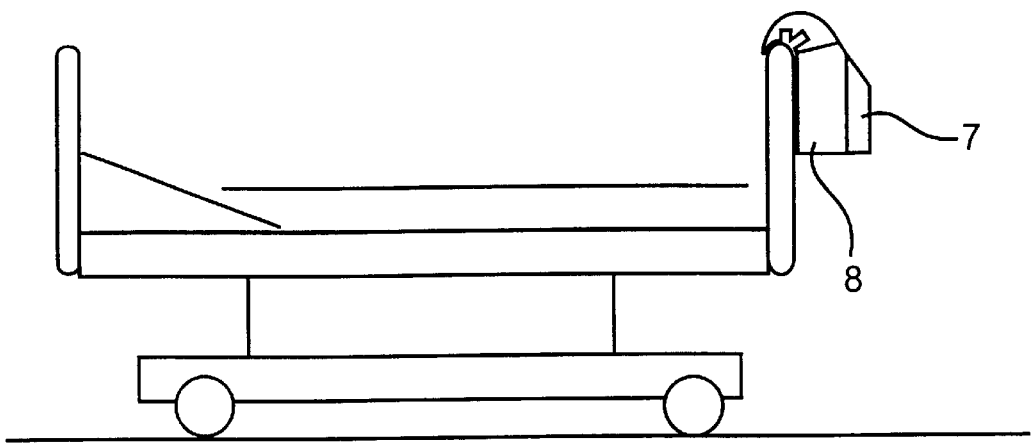
FIG. 14B is a sectional view of the terminal that is held on a circular tube with the carrying device and also showing the position of the patients bed.

Furthermore, the strut 82 is provided with a second recess 85, which is used for placement on a horizontal circular tube 111. The second recess 85 is shaped such that it surrounds the circular tube 111 to the extent that it holds the terminal 8 on the circular tube when the housing of the terminal 8 is supported at least at another point in the vertically hanging position, as is shown in FIGS. 14A and 14B. The terminal 8 is shown in FIG. 14B with the transport display module 7 attached suspended at the foot end of the hospital bed.

Figure 12:
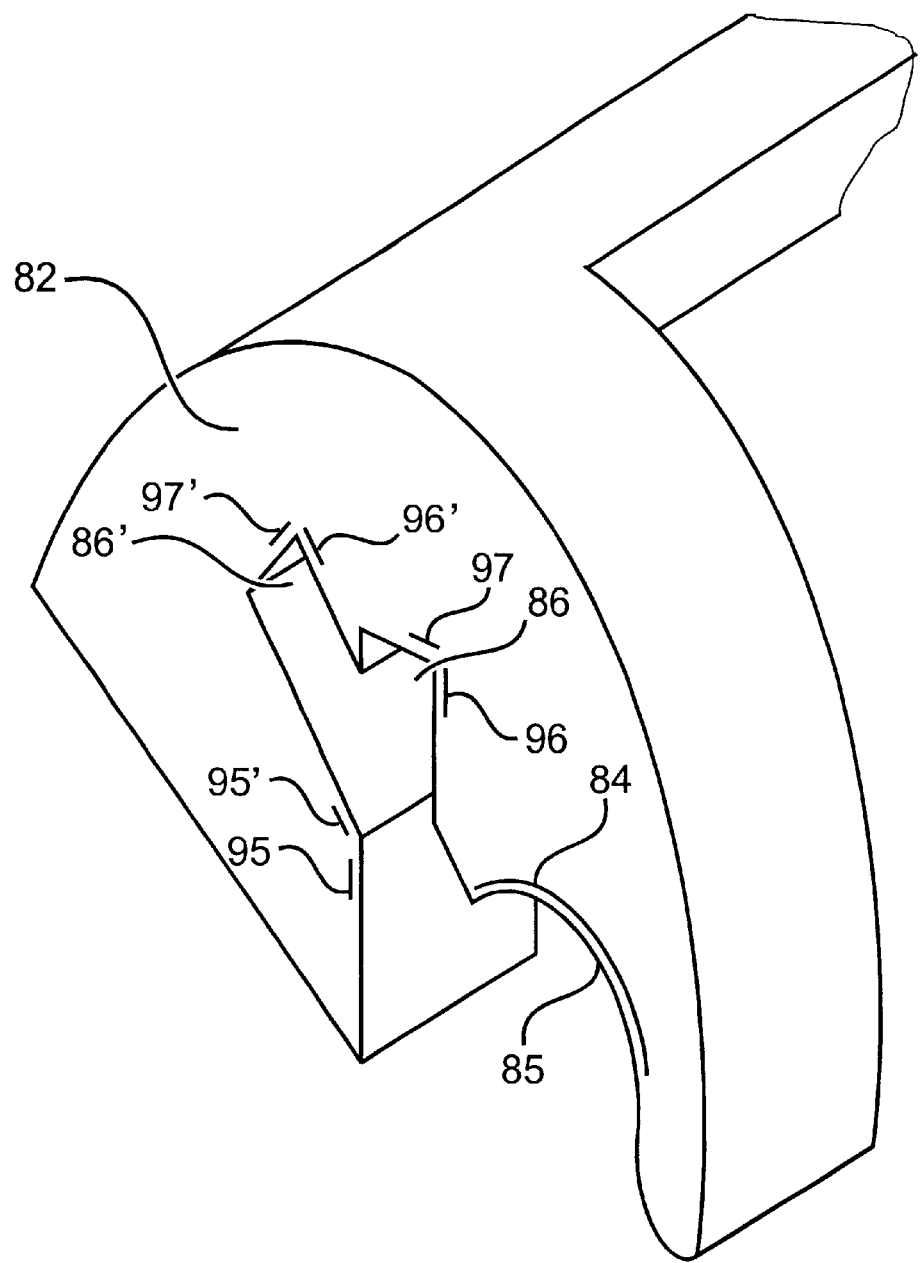
FIG. 12 is a perspective view of a strut of the carrying device of the terminal.

FIG. 12 shows a more detailed representation of the arrangement of the recesses.86, 86' and 85 on the strut 82. The first recess 86 has a rectangular cross section of a shape complementary to the cross section of the fastening rail 110 and when it is placed on the fastening rail 110, it offers contact surfaces 95, 96 and 97. The contact surfaces 95, 96 preferably have a minimum length of 4 mm each. The corresponding contact surface 97 preferably has a minimum length of 2.5 mm.

The other first recess 86', which is arranged at the bottom at an angle 98 to the vertical, offers contact surfaces 95', 96' and 97', which should be dimensioned corresponding to the contact surfaces 95, 96 and 97.

Figure 15B:
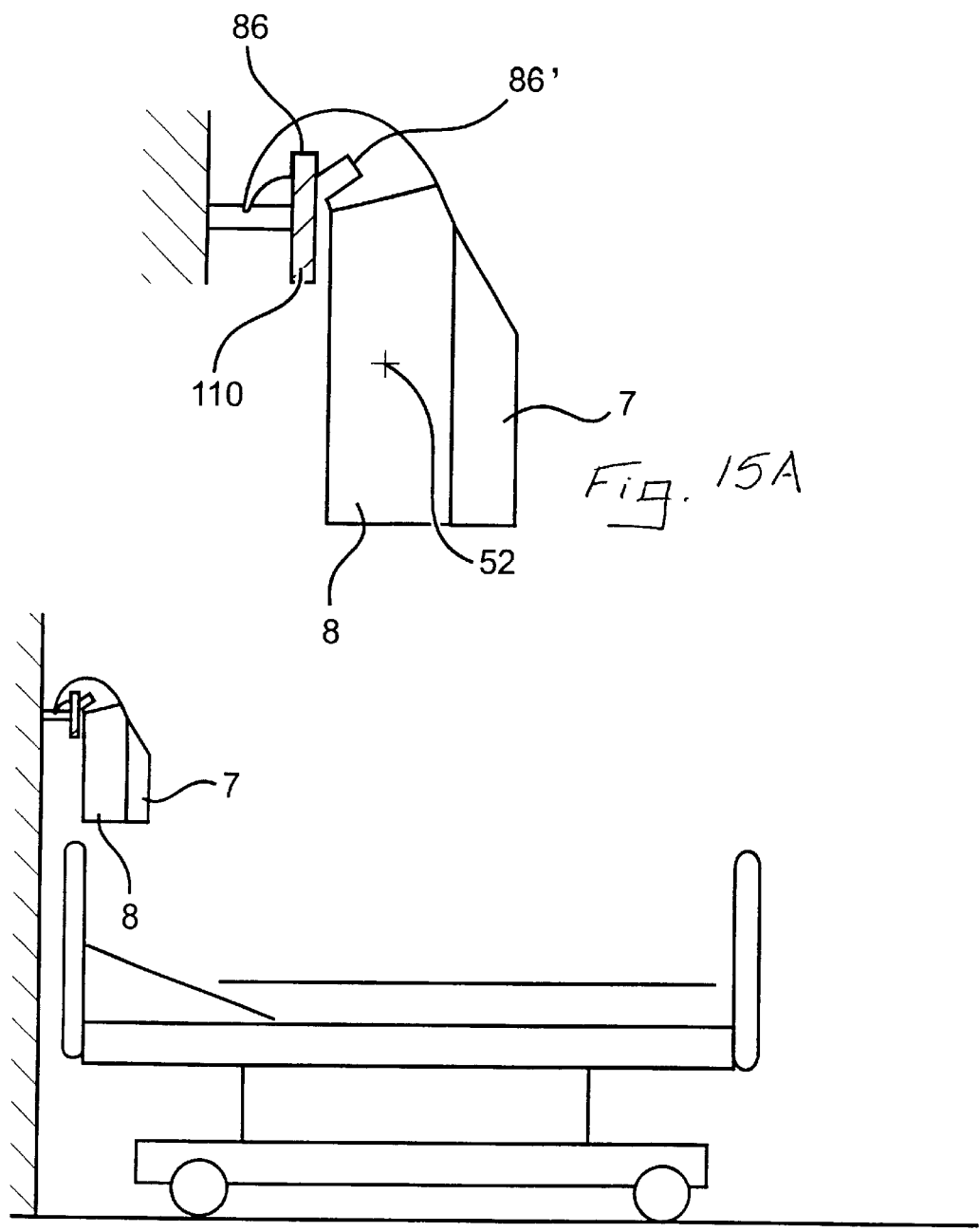
FIG. 15B is a sectional side view of the terminal that is held on a rail in the vertical position with the carrying device and also showing the position of the patients bed.

At least the first recess 86 is preferably arranged on the strut 82 such that in the projection 81 to the horizontal plane, it is located outside the projected base 90 of the housing 17 of the terminal 8, which base is schematically shown in FIG. 10. It is ensured as a result that when the terminal 8 is suspended on a fastening rail 110 with the carrying device in the vertically hanging position, as is shown in FIGS. 15A and 15B, it will be held at a spaced location from the fastening rail 110.

While specific embodiments of the invention have been shown and described in detail to illustrate the application of the principles of the invention, it will be understood that the invention may be embodied otherwise without departing from such principles.

What is claimed is:

1. A patient monitoring device for connection with sensors, comprising:

a transportable terminal with a housing, connections for connection to said sensors for measuring physical parameters of the patient, signal processing devices for receiving and processing the sensor signals received, as well as with a network adapter for forwarding the processed sensor data to a stationary medical workplace, the stationary medical workplace having a display and an alarm device, said transportable terminal electrical contacts;

a transport display module with electrical contacts which are complementary to said transportable terminal electrical contacts; and an expansion module with electrical contacts which are complimentary to said transportable terminal electrical contacts said expansion module being provided for the connection of said additional desired sensors, in which said housing of said transportable terminal is provided on one side with a connection mechanism for the positive-locking coupling of the transport display module and on another side with a connection mechanism for the positive-locking coupling of said expansion module for receiving signals of said additional sensors, the transportable terminal electrical contacts coming into connection with said transport display module electrical contacts and on said expansion module electrical contacts at the time of the coupling of the respective connection mechanism to establish an electric connection.

2. The patient monitoring device in accordance with claim 1, wherein said housing of said transportable terminal is a substantially flat component and said connection mechanism for positive-locking coupling of said expansion module and of said transport display module are arranged on opposite large-area side faces of said housing.

3. The patient monitoring device in accordance with claim 1, wherein a side of said expansion module that faces away from said transportable terminal in a coupled position of said first expansion module is provided with a connection mechanism corresponding to said connection mechanism on said transportable terminal so that an additional expansion module can be coupled with said expansion module in the same manner as directly with the terminal.

4. The patient monitoring device in accordance with claim 1, wherein said connection mechanism for the positive-locking coupling with the housings has a guide pair each guide comprising either a guide support on the transportable terminal and a complementary guide body on the expansion module and the transport display module or a guide support on said expansion module and said transport display module and a guide body on the transportable terminal, said guide pairs being designed such that said guide pairs can be brought into engagement with one another with the terminal standing upright by depositing the transport display module and the expansion module downward in the vertical direction.

5. The patient monitoring device in accordance with claim 4, wherein said guide body and the guide support are designed such that they make possible the pivoting of the guide body in the guide support, wherein the pivot axis extends at right angles to the vertical direction and in parallel to the surface of the housing of the transportable terminal.

6. The patient monitoring device in accordance with claim 5, wherein said guide support and said guide body of each connection mechanism are provided with a groove and a tongue, which engage one another during insertion, wherein the groove is designed as a one-sided undercut in said housing surface such that with said tongue inserted, said guide body can be pivoted in relation to said guide support around a pivot axis defined by a longitudinal axis of said groove.

7. The patient monitoring device in accordance with claim 5, wherein said guide body and said guide support are arranged such that said pivot axis is located under a center of gravity of said terminal.

8. The patient monitoring device in accordance with claim 5, wherein said connection mechanisms for the positive-locking coupling also have a centering pair each comprising either a centering body on said transportable terminal and a complementary centering fit on said expansion module and on said transport display module or a centering fit on said transportable terminal and a centering body on said expansion module and on said transport display module, so that said centering body is pushed into a centering fit during the pivoting of said transport display module or of said expansion module in the direction of a coupled position with said transportable terminal, and bring about a centering into a desired coupled position due to their complementary conical design.

9. The patient monitoring device in accordance with claim 1, wherein said guide support on said terminal comprises a recess in the housing wall, which is sloped in relation to said housing surface, deepens downward in a vertical direction in said vertical position of said terminal, and cooperates with a complementary, downwardly rising projection acting as a guide body on said transport display module, wherein said groove and tongue are arranged on lower end sides of said recess and of said projection, respectively.

10. The patient monitoring device in accordance with claim 9, wherein each said guide recess in said housing wall has side walls, which taper downward in a vertical direction and are essentially vertical in relation to a surface of the housing wall, and each said guide body has correspondingly tapering complementary side walls, which cooperate to guide and center the connection mechanism.

11. The patient monitoring device in accordance with claim 1, wherein each connection mechanism also has a claw, which can be detachably locked in a locking mechanism of an opposing flank on another part in the coupled position.

12. The patient monitoring device in accordance with claim 1, wherein said housing of said transportable terminal and said parts of said connection mechanisms are made of plastic.

13. The patient monitoring device in accordance with claim 1, wherein said transportable terminal is provided with a projection, which laterally projects beyond the connection mechanisms and the contact area with the transport display module and is provided with display and operating elements for control or data entry.

14. The patient monitoring device in accordance with claim 1, wherein said transportable terminal is provided with a carrying device, which has a transport grip extending horizontally above said transportable terminal and fastened to said transportable terminal with at least one strut.

15. The patient monitoring device in accordance with claim 14, wherein said strut of said carrying device has a contour forming at least one first recess in its contour for receiving a horizontal, polygonal fastening rail in a positive-locking manner and at least one second recess for placement on a horizontal circular tube.

16. The patient monitoring device in accordance with claim 15, wherein said first recess is arranged such that said transportable terminal is aligned essentially vertically when it is suspended with said first recess in a horizontal fastening rail.

17. The patient monitoring device in accordance with claim 15, wherein said additional first recess is arranged such that said terminal is aligned obliquely to a vertical, especially at an angle of about 30° to 60° and preferably about 45° when it is suspended with the additional first recess in the horizontal fastening rail.

18. The patient monitoring device in accordance with claim 15, wherein said strut, of which there is at least one, is arranged on a housing of said transportable terminal such that with the terminal standing upright, it extends beyond a projected base of the housing of said transportable terminal (8) in the projection into the horizontal plane.

19. The patient monitoring device in accordance with claim 16, wherein said first recess is rectangular, complementary to the profile of the fastening rail and is provided, with the terminal standing upright, with two, essentially vertically extending side faces and with a horizontally extending top side and is arranged on a strut such that it is located in the projection outside said base of said housing of said transportable terminal.

20. The patient monitoring device in accordance with claim 17, wherein said additional first recess is rectangular, complementary to a profile of the fastening rail and is provided, with said terminal standing upright, with two side faces extending obliquely in relation to the vertical and with a top side that extends at right angles thereto and is arranged on a strut such that in the projection into the horizontal plane, it is located at least partially within a base of the housing of the terminal.

21. The patient monitoring device in accordance with claim 15, wherein second recess for placement on a horizontal circular tube is shaped on strut such that it surrounds the circular tube to the extent that, with the housing being supported in a vertically suspended position, it holds the terminal on the circular tube at least at one additional point.

22. The patient monitoring device in accordance with claim 15, in which said two parallel struts are present, which carry the transport grip between them.

23. The patient monitoring device in accordance with claim 22, wherein said struts are arranged on a top side of said housing of said transportable terminal on opposite sides of said housing.

24. A patient monitoring system, comprising:
a sensor;
a stationary medical workplace having a display and an alarm device;
a transportable terminal with a housing, connections for connection to said sensors for measuring physical parameters of the patient, signal processing devices for receiving and processing the sensor signals received, as well as with a network adapter for forwarding the processed sensor data to said stationary medical workplace, said housing having a surface with a transport terminal display connection mechanism and transport terminal display electrical contacts and having another surface with an expansion module connection mechanism and transport terminal expansion module electrical contacts;

a transport display module with display electrical contacts which are complementary to said transport terminal display electrical contacts of said transportable terminal and having a transport display complementary portion for the positive-locking coupling of said transport display module and said housing;

an expansion module with expansion electrical contacts which are complementary to said transportable terminal expansion electrical contacts and having an expansion module complementary portion for the positive-locking coupling of said expansion module and said housing, said expansion module including a sensor connection for receiving sensor signals, said transportable terminal display electrical contacts coming into connection with said transport display module electrical contacts at the time of a coupling of said transport display complementary portion with said transport terminal display connection mechanism to establish an electrical connection between said transportable terminal and said transportable terminal display and said transportable terminal expansion module electrical contacts coming into connection with said expansion module electrical contacts at the time of a coupling of said transport expansion module complementary portion with said transport terminal expansion module connection mechanism to establish an electrical connection between said transportable terminal and said expansion module.

25. The patient monitoring device in accordance with claim 24, further comprising:

a sensor connection at said transportable terminal; and another sensor, wherein at least one of said sensors is connected to said transportable terminal and said another at least one of said sensors is connected to said expansion module.

26. A patient monitoring device comprising:

a transportable terminal with a housing, sensor connections for measuring physical parameters of the patient, signal processing devices for receiving and processing the sensor signals received, a network adapter for forwarding the processed sensor data, said housing having a first side with a transport terminal display connection mechanism and transport terminal display electrical contacts and having a second side with an expansion module connection mechanism and transport terminal expansion module electrical contacts;

a transport display module with display electrical contacts which are complementary to said transport terminal display electrical contacts of said transportable terminal and having a transport display complementary portion for the positive-locking coupling of said transport display module and said housing;

an expansion module with expansion electrical contacts which are complementary to said transportable terminal expansion electrical contacts and having an expansion module complementary portion for the positive-locking coupling of said expansion module and said housing, said expansion module including a sensor connection for receiving sensor signals, said transportable terminal display electrical contacts coming into connection with said transport display module electrical contacts at the time of a coupling of said transport display complementary portion with transport terminal display connection mechanism to establish an electric connection between said transportable terminal and said transportable terminal display and said transportable terminal expansion module electrical contacts coming into connection with said expansion module electrical contacts at the time of a coupling of said transport expansion module complementary potion with transport terminal expansion module connection mechanism to establish an electric connection between said transportable terminal and said expansion.

\* \* \* \* \*